(12) United States Patent
Madabhushi et al.

(10) Patent No.: US 11,055,844 B2
(45) Date of Patent: Jul. 6, 2021

(54) PREDICTING RESPONSE TO IMMUNOTHERAPY USING COMPUTER EXTRACTED FEATURES OF CANCER NUCLEI FROM HEMATOXYLIN AND EOSIN (HANDE) STAINED IMAGES OF NON-SMALL CELL LUNG CANCER (NSCLC)

(71) Applicant: Case Western Reserve University, Cleveland, OH (US)

(72) Inventors: Anant Madabhushi, Shaker Heights, OH (US); Xiangxue Wang, Cleveland Heights, OH (US); Cristian Barrera, Cleveland, OH (US); Vamsidhar Velcheti, Pepper Pike, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 47 days.

(21) Appl. No.: 16/281,324

(22) Filed: Feb. 21, 2019

(65) Prior Publication Data
US 2019/0259154 A1 Aug. 22, 2019

Related U.S. Application Data

(60) Provisional application No. 62/633,342, filed on Feb. 21, 2018.

(51) Int. Cl.
*G06K 9/00* (2006.01)
*G06T 7/00* (2017.01)
(Continued)

(52) U.S. Cl.
CPC .......... *G06T 7/0012* (2013.01); *G06K 9/0014* (2013.01); *G06K 9/00147* (2013.01);
(Continued)

(58) Field of Classification Search
CPC ......... G06T 7/0012; G06T 2207/30024; G06T 2207/10056; G06T 2207/30096;
(Continued)

(56) References Cited

U.S. PATENT DOCUMENTS

| | | | | |
|---|---|---|---|---|
| 2001/0050999 | A1* | 12/2001 | Bacus, V | G06T 7/0012 382/128 |
| 2013/0094750 | A1* | 4/2013 | Tasdizen | G06K 9/0014 382/134 |
| 2017/0193657 | A1* | 7/2017 | Madabhushi | G06K 9/3233 |

* cited by examiner

*Primary Examiner* — Alex Kok S Liew
(74) *Attorney, Agent, or Firm* — Eschweiler & Potashnik, LLC

(57) ABSTRACT

Embodiments access a digitized image of tissue demonstrating non-small cell lung cancer (NSCLC), the tissue including a plurality of cellular nuclei; segment the plurality of cellular nuclei represented in the digitized image; extract a set of nuclear radiomic features from the plurality of segmented cellular nuclei; generate at least one nuclear cell graph (CG) based on the plurality of segmented nuclei; compute a set of CG features based on the nuclear CG; provide the set of nuclear radiomic features and the set of CG features to a machine learning classifier; receive, from the machine learning classifier, a probability that the tissue will respond to immunotherapy, based, at least in part, on the set of nuclear radiomic features and the set of CG features; generate a classification of the tissue as a responder or non-responder based on the probability; and display the classification.

20 Claims, 13 Drawing Sheets

(51) Int. Cl.

| | |
|---|---|
| *G06K 9/46* | (2006.01) |
| *G06T 7/40* | (2017.01) |
| *G06T 7/62* | (2017.01) |
| *G06K 9/62* | (2006.01) |
| *G06T 7/11* | (2017.01) |
| *G16H 30/40* | (2018.01) |
| *G16H 50/20* | (2018.01) |

(52) U.S. Cl.
CPC ........... *G06K 9/469* (2013.01); *G06K 9/6257* (2013.01); *G06K 9/6262* (2013.01); *G06K 9/6267* (2013.01); *G06T 7/11* (2017.01); *G06T 7/40* (2013.01); *G06T 7/62* (2017.01); *G16H 30/40* (2018.01); *G16H 50/20* (2018.01); *G06K 2209/05* (2013.01); *G06T 2207/10056* (2013.01); *G06T 2207/20072* (2013.01); *G06T 2207/20076* (2013.01); *G06T 2207/20081* (2013.01); *G06T 2207/30024* (2013.01); *G06T 2207/30061* (2013.01); *G06T 2207/30096* (2013.01)

(58) Field of Classification Search
CPC ............. G06T 2207/20081; G06T 7/11; G06T 7/0014; G06T 2207/30068; G06T 2207/10024; G06T 2207/20064; G06T 2207/10088; G06T 2207/20084; G06T 7/42; G06T 11/60; G06T 2207/10048; G06T 2207/10072; G06T 2207/10132; G06T 2207/20021; G06T 2207/20072; G06T 2207/20104; G06T 2207/30088; G06T 5/002; G06T 7/90; G06K 9/00147; G06K 9/00127; G06K 9/0014; G06K 9/6212; G06K 9/00; G06K 9/6247; G06K 9/628; G06K 9/00134; G06K 9/4642

See application file for complete search history.

PREDICTING RESPONSE TO IMMUNOTHERAPY USING COMPUTER EXTRACTED FEATURES OF CANCER NUCLEI FROM HEMATOXYLIN AND EOSIN (HANDE) STAINED IMAGES OF NON-SMALL CELL LUNG CANCER (NSCLC)

CROSS REFERENCE TO RELATED APPLICATIONS

This application claims the benefit of U.S. Provisional Application 62/633,342 filed Feb. 21, 2018, which is incorporated by reference herein in its entirety.

FEDERAL FUNDING NOTICE

This invention was made with government support under the grant(s): 1U24CA199374-01, R01CA202752, R01CA202752-01A1, R01CA208236-01A1, R21CA179327-01, R21CA195152-01, R01 DK098503-02, 1 C06 RR12463-01 and NIH T32EB007509, awarded by the National Institutes of Health. Also PC120857, LC130463, and W81XWH-16-1-0329 awarded by the Department of Defense. The government has certain rights in the invention.

BACKGROUND

Immune checkpoint inhibitors are used in treating advanced stage non-small cell lung cancer (NSCLC). These drugs, including Nivolumab, target the programmed cell death protein 1 (PD-1) receptor or its ligand PD-L1. However, patients treated with immune checkpoint inhibitors have a response rate of only approximately 20%. The current gold standard biomarker, detection of tissue-based PD-L1 expression, is inadequate. It is thus crucial to identify which patients will derive maximal benefit from such treatments.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
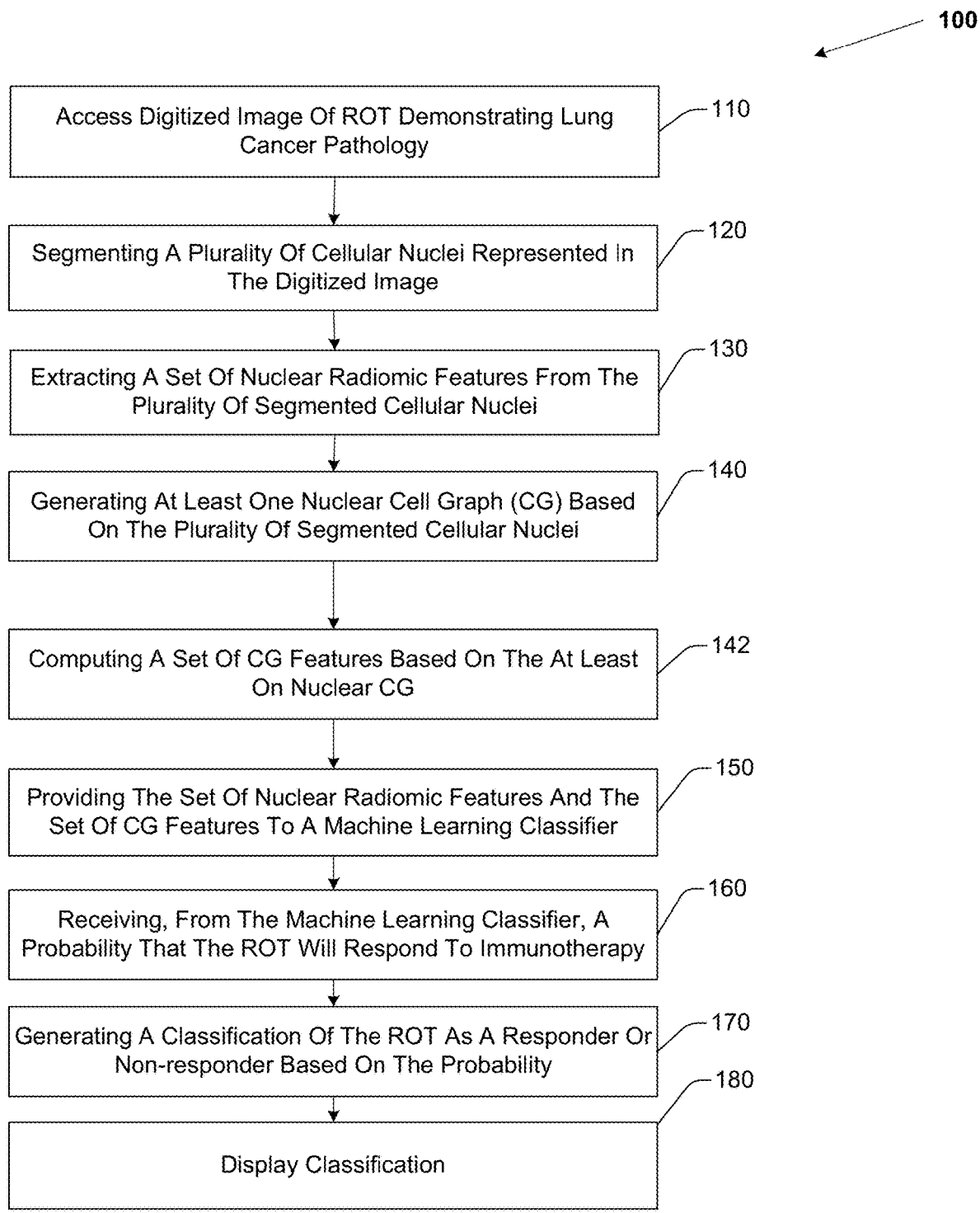
FIG. 1 illustrates example operations for predicting response to immunotherapy in NSCLC.

Embodiments predict response to immunotherapy in non-small cell lung cancer (NSCLC). Embodiments access a digitized hematoxylin and eosin (H&E) stained image of a region of tissue demonstrating NSCLC. The region of tissue includes a plurality of cellular nuclei. Embodiments may segment nuclear boundaries using a deep learning approach.

Embodiments extract a set of nuclear shape features and texture features from segmented cellular nuclei represented in the digitized H&E stained imagery of the region of tissue. The set of nuclear shape features and texture features may include a nuclear size feature, a nuclear area feature, a nuclear axis length feature, a nuclear perimeter feature, or a nuclear texture feature. Nuclear texture features may include, for example, a Haralick feature.

Embodiments further construct a nuclear cell graph (CG) based on the cellular nuclei represented in the digitized H&E stained image. In one embodiment, the cell graph is a global cell graph in which each nucleus represented in the digitized H&E stained image defines a node of the graph. Embodiments may define nodes on all the cellular nuclei represented in the digitized H&E image. Thus, embodiments may define nodes of the CG on different types of nuclei. For example, embodiments may define nodes on cancer cell nuclei and on tumor infiltrating lymphocytes, or on other types of cellular nuclei. Nodes may be connected based on distance metrics such as Euclidean Distance between nodes, or the L1 norm. In another embodiment, a threshold number of nuclei (e.g., 50%, 75%, or 90%) represented in the digitized H&E stained image may be employed to define nodes of the graph. The threshold number of nuclei may be user selectable, may be defined according to available computational resources, or may be defined according to a desired level of predictive accuracy.

Embodiments quantitatively evaluate the spatial arrangement of nuclei through the construction of a CG or CGs. A graph is a mathematical construct comprising of a finite sets of objects (nodes) that capture global and local relationships via pair-wise connections (edges) between the nodes. Graphs may be used to quantitatively characterize nuclear architecture in histopathological images by representing the nuclei as nodes and subsequently quantifying neighborhood relationships (e.g., proximity) and spatial arrangement between the nodes.

Embodiments represent centroids of each of, or a threshold number of, the cellular nuclei represented in the image as nodes of a graph. Nodes may be connected to others based on a weighted Euclidean norm where a weighting function favors connectivity between proximal nodes. In existing approaches, this may result in multiple disconnected subgraphs being generated. Embodiments construct a global CG without disconnected subgraphs. The threshold number of nuclei defined as nodes of a graph, may be selected based on a desired level of predictive accuracy, or on a desired use of computational resources, or on other criteria.

Embodiments compute a set of cell graph features based on the CG. The set of cell graph features capture tumor morphology within the microenvironment of the tumor. These features may include first-order statistics (e.g. mean, mode, median) of the representative descriptors. In one embodiment, the set of cell graph features may include a Delaunay side length disorder of the cells feature. The set of cell graph features may also include a Delaunay ratio of the minimum and maximum triangular areas formed by cells feature. The set of cell graph features may also include a number of possible triangles formed from cells (i.e., nodes) of the cell graph feature. Other cell graph features may be computed.

Embodiments provide the set of nuclear shape features and texture features, and the set of cell graph features, to a machine learning classifier trained to distinguish tissue that will respond to immunotherapy from tissue that will not respond to immunotherapy. In one embodiment, the machine learning classifier is a quadratic discriminant analysis (QDA) classifier. Embodiments receive a probability of response computed by the machine learning classifier. The machine learning classifier computes the probability based on the set of nuclear shape features and texture features, and the set of cell graph features. Embodiments classify the region of tissue as likely to experience response to immunotherapy, or unlikely to experience response to immunotherapy, based, at least in part, on the probability of response. Immunotherapy may include Nivolumab immunotherapy, pembrolizumab, atezolizumab, or other type of checkpoint inhibitor immunotherapy. Response may include pathological complete response (pCR), or other type of response.

In one embodiment, digitized images of pre-treatment H&E stained tissue slides of pre-treatment tumor biopsies are acquired of a cohort of fifty six (56) patients, from two different institutions. The patients demonstrate NSCLC and were treated with Nivolumab or other form of NSCLC immunotherapy. The cohort of 56 patients was split into two categories: responders, and non-responders. Membership in a category (e.g., responder, non-responder) was determined by clinical involvement and radiological assessment using the RECIST criteria. In another embodiment, membership in a category (e.g., responder, non-responder) may be determined using another, different criteria. In one embodiment, the cohort is randomly divided into a training set (n=32) and a testing set (n=24). In one embodiment, 245 radiomic features were extracted from tumor nuclei, and included features that characterize shape and texture of the tumor nuclei represented in the digitized images. Nuclei may be annotated automatically, using for example, a deep learning approach or a watershed approach, or manually by expert human pathologists on the digitized H&E images.

Figure 5:
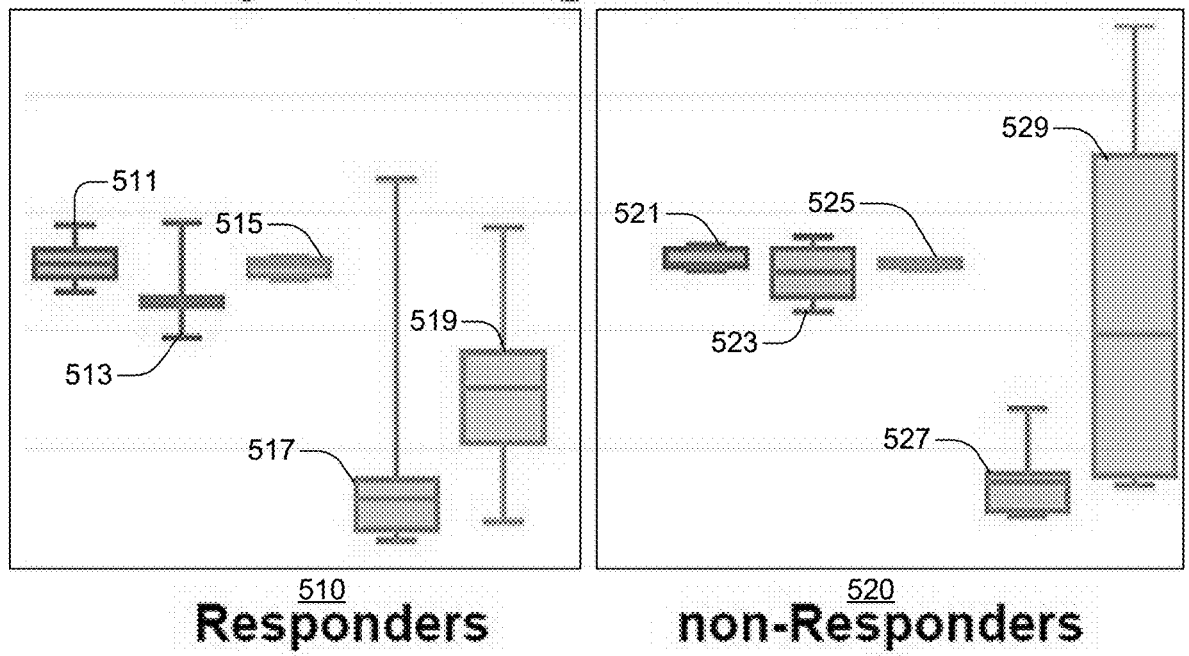
FIG. 5 is a box-plot graph of discriminative features.

A statistical feature selection method was employed to determine the top five most discriminative features from the training set. In one embodiment, a minimum redundancy, maximum relevance (mRMR) feature selection technique is employed. In another embodiment, other feature selection techniques may be employed. The top five features in this embodiment capture the spatial arrangement of nuclei and variance in nuclear shape and chromatin structure. FIG. 5 illustrates box plots 510 and 520. Box plot 510 illustrates the top five most significant (i.e., discriminative) features associated with responders. The vertical axes in box plots 510 and 520 represent the continuous feature values shown as a distribution over the sample population. Box plot 510 includes plots for a side length disorder of a Delaunay triangulation feature 511, a ratio of minimum and maximum triangular areas formed by nodes of the CG 517, and a number of possible polygons formed by nodes of the CG 519. Box plot 510 also includes plots for a standard deviation of the fractal dimension of a nucleus feature 513, and a mean of a tensor contrast entropy of cellular nuclei feature 515. Box plot 520 illustrates the top five most significant (i.e., discriminative) features associated with non-responders Box plot 520 includes plots for a side length disorder of a Delaunay triangulation feature 521, a ratio of minimum and maximum triangular areas formed by nodes of the CG 527, and a number of possible polygons formed by nodes of the CG 529. Box plot 520 also includes plots for a standard deviation of the fractal dimension of a nucleus feature 523, and a mean of a tensor contrast entropy of cellular nuclei feature 525.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 is a flow diagram of example operations 100 that may be performed by a processor to predict response to immunotherapy in NSCLC. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 includes, at 110, accessing a digitized image of a region of tissue (ROT) demonstrating cancerous pathology. The ROT includes a plurality of cellular nuclei. The digitized image includes a plurality of pixels, a pixel having an intensity. In one embodiment, the digitized image is a digitized image of a H&E stained slide of region of tissue demonstrating non-small cell lung cancer (NSCLC) scanned at 20× magnification. While digitized H&E images scanned at 20× magnification are described in this example, images having other imaging parameters or acquired using other imaging modalities may be employed. Accessing the digitized image includes acquiring electronic data, reading from a computer file, receiving a computer file, reading from a computer memory, or other computerized activity not practically performed in a human mind.

Figure 2:
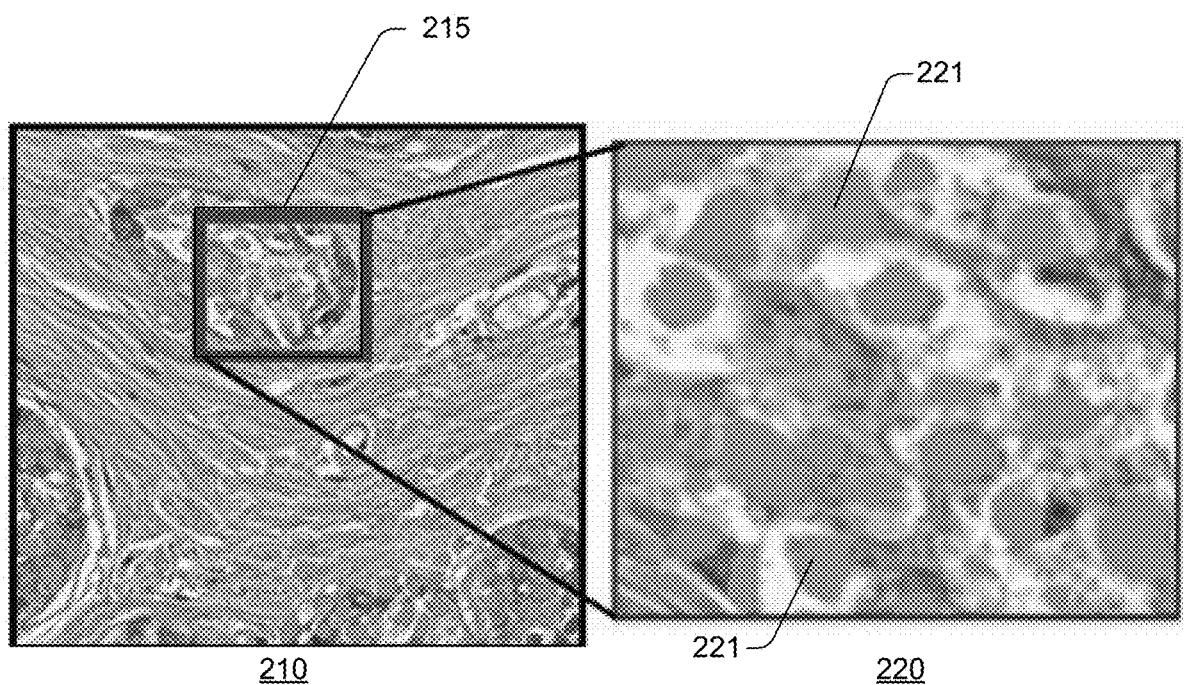
FIG. 2 illustrates segmented cellular nuclei in NSCLC tissue.

Operations 100 also includes, at 120, segmenting a plurality of cellular nuclei represented in the digitized image. In one embodiment, segmenting the plurality of cellular nuclei represented in the digitized image includes segmenting the plurality of cellular nuclei using a deep learning approach. For example, embodiments may employ a convolutional neural network (CNN) configured to segment nuclei from non-nuclei portions of the digitized image. Segmenting the plurality of cellular nuclei includes acquiring electronic data, reading from a computer file, receiving a computer file, reading from a computer memory, or other computerized activity not practically performed in a human mind. FIG. 2 illustrates a region of tissue 210 demonstrating NSCLC. FIG. 2 further illustrates a sub-section 215 of the region of tissue 210. A magnified view 220 of subsection 215 further illustrates segmented cellular nuclei 221. In embodiments described herein, segmented cellular nuclei 221 may be, for example a cancerous nucleus, a tumor infiltrating lymphocyte (TIL), or other type of cellular nucleus.

In one embodiment, a watershed-based technique is used for automatically detecting and segmenting members of the plurality of cellular nuclei represented in the digitized image. This technique applies a set of mathematical operations, including fast radial symmetry transform and regional minima, at different scales (e.g., 5×, 10× and 20×) to identify candidate locations for nuclei. This technique improves on those employed by existing approaches to segmenting nuclei by being computationally simpler and faster. This technique also facilitates the adjustment and fine-tuning of parameters with greater simplicity than techniques used by existing approaches, thereby providing the technical effect of improving the performance of computers, systems, or other apparatus on which embodiments are implemented. In one embodiment, cellular nuclei represented in the digitized H&E image are already segmented, and thus in one embodiment, the operations at 120 may not need to be performed.

Figure 3:
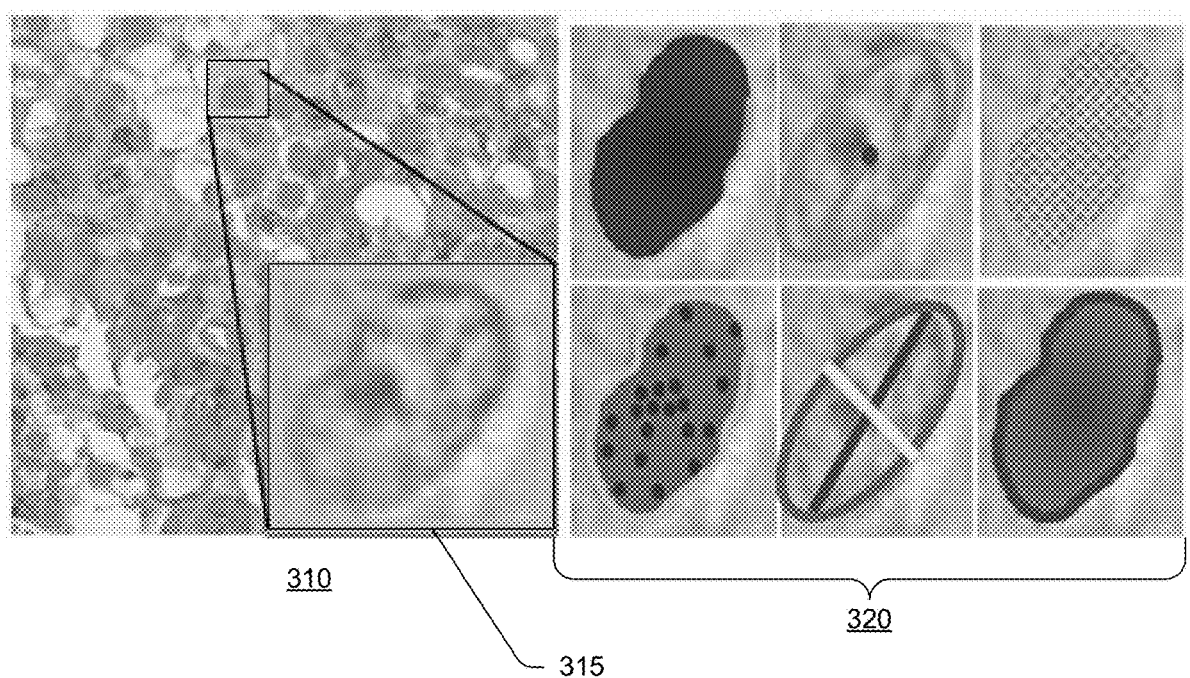
FIG. 3 illustrates nuclear shape and texture features.

Operations 100 also includes, at 130, extracting a set of nuclear radiomic features from the plurality of segmented cellular nuclei. In one embodiment, the set of nuclear radiomic features includes at least one of a nuclear size feature, a nuclear area feature, a nuclear axis length feature, a nuclear perimeter feature, or a nuclear texture feature. In one embodiment, the set of nuclear radiomic features includes a standard deviation of the fractal dimension of a nucleus feature, and a mean of a tensor contrast entropy of a cellular nuclei feature. Extracting the set of nuclear radiomic features includes acquiring electronic data, reading from a computer file, receiving a computer file, reading from a computer memory, or other computerized activity not practically performed in a human mind. FIG. 3 illustrates a region of tissue 310 demonstrating NSCLC. Region of tissue 310 includes a plurality of cellular. A magnified view of a member of the plurality of cellular nuclei 315 is illustrated. Nuclear radiomic features (e.g., shape features, texture features) associated with the member of the plurality of cellular nuclei 315 are illustrated at 320.

Figure 13:
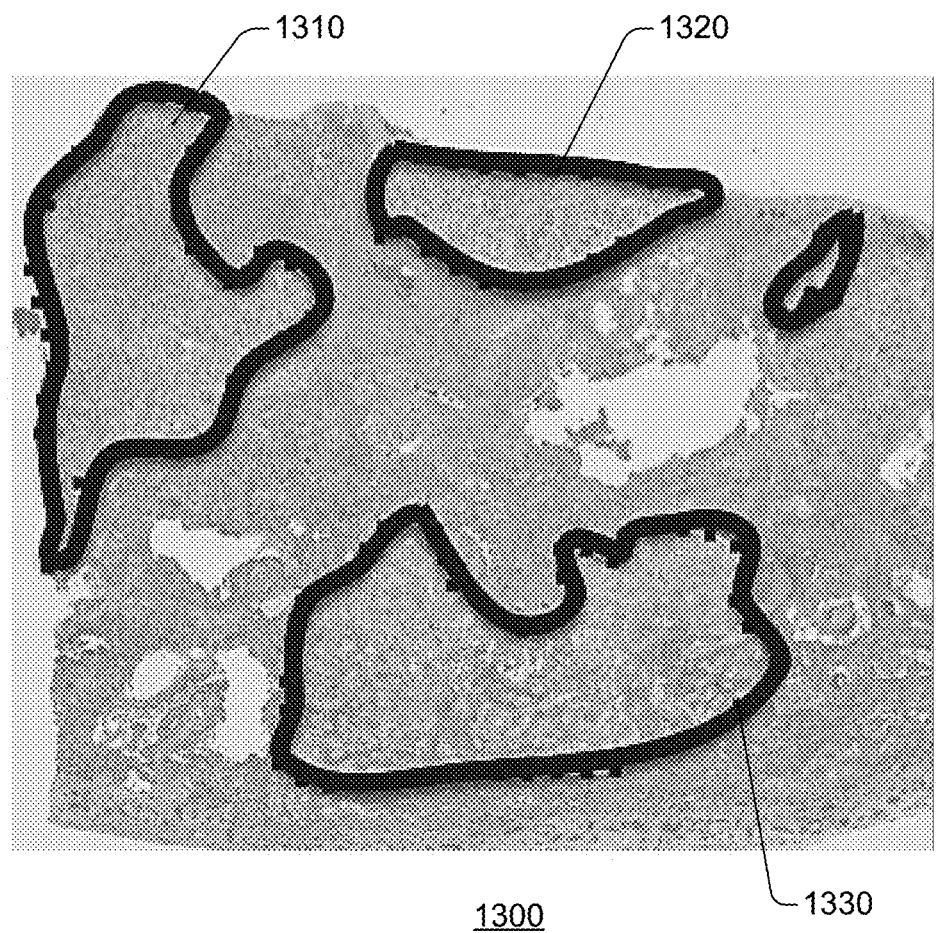
FIG. 13 illustrates regions of tissue demonstrating NSCLC.

Operations 100 also includes, at 140, generating at least one nuclear cell graph (CG) based on the plurality of segmented cellular nuclei. In one embodiment, a node of the at least one nuclear CG is defined on a centroid of a member of the plurality of cellular nuclei. A first node is connected to a second, different node based on a Euclidean distance between the first node and the second node. In another embodiment, the centroid of a local nuclei cluster is used as a node, and a plurality of nodes is used to construct the global CG. The probability a first node will be linked with a second, different node is based on an exponentially decaying function of the Euclidean distance between the nodes. In one embodiment, the at least one nuclear CG is a global CG. In another embodiment, the digitized image may include more than one tumor region. In that case, where there is more than one tumor region represented in the digitized image, embodiments may construct more than one CG. For example, embodiments may construct one CG for each tumor region, respectively. FIG. 13 illustrates a region of tissue 1300. Region of tissue 1300 includes more than one tumor region. For example, region of tissue includes a first tumor region 1310, a second, different tumor region 1320, and third, different tumor region 1330. Generating the at least one nuclear CG includes acquiring electronic data, reading from a computer file, receiving a computer file, reading from a computer memory, or other computerized activity not practically performed in a human mind.

Operations 100 also includes, at 142, computing a set of CG features based on the at least one nuclear CG. In one embodiment, the set of CG features includes at least one of a Delaunay triangulation feature or a Voronoi feature. In one embodiment, the set of CG features includes a side length disorder of a Delaunay triangulation feature, a ratio of minimum and maximum triangular areas formed by nodes of the CG, and a number of possible polygons formed by nodes of the CG. In this embodiment, a polygon is a triangle. Computing the set of CG features includes acquiring electronic data, reading from a computer file, receiving a computer file, reading from a computer memory, or other computerized activity not practically performed in a human mind.

Figure 4:
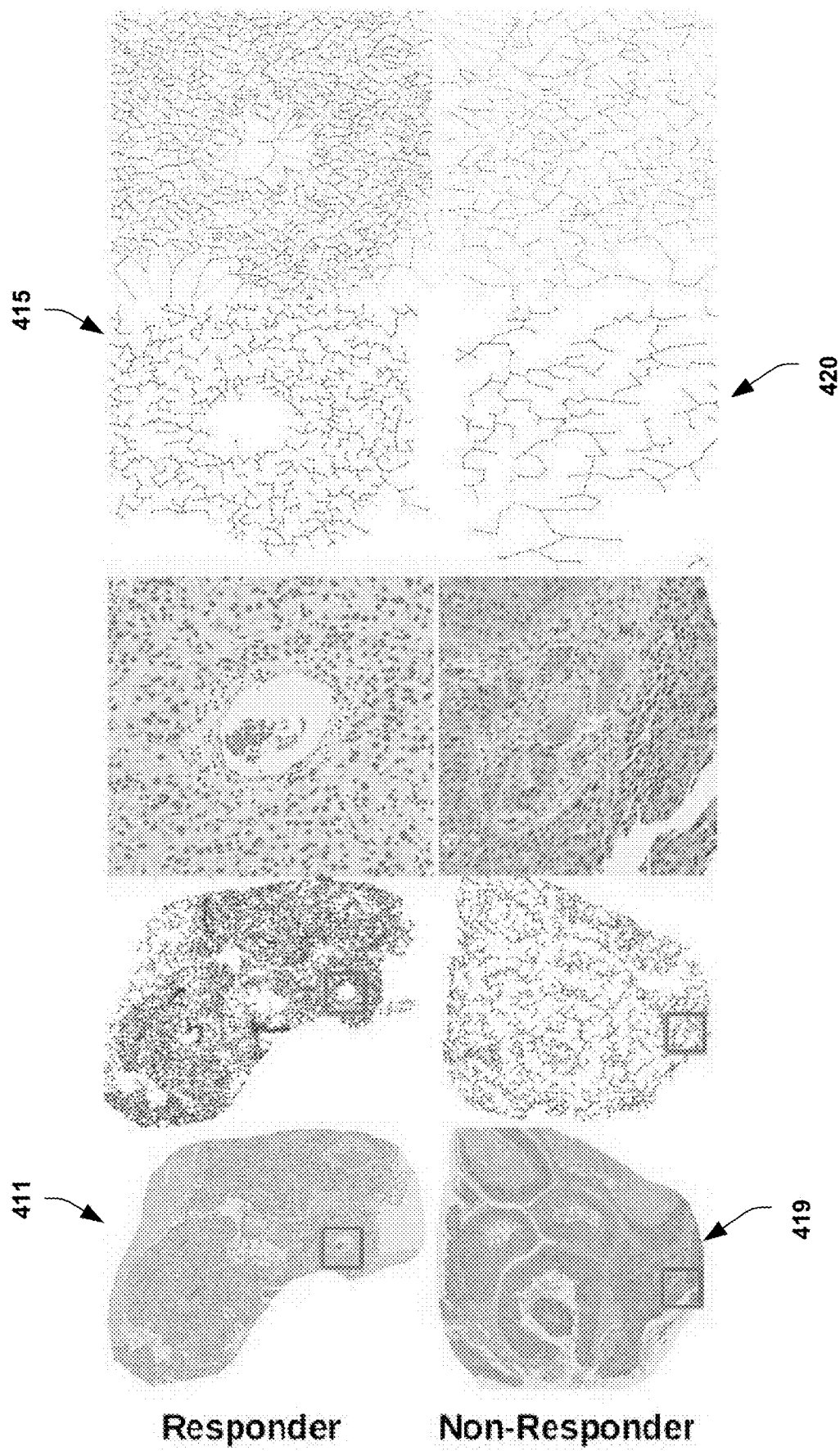
FIG. 4 illustrates cellular nuclei graphs in NSCLC tissue.

FIG. 4 illustrates cellular nuclei graphs in NSCLC tissue. A region of tissue 411 that responded to immunotherapy is illustrated. Region of tissue 411 includes a plurality of cellular nuclei. A global nuclear CG 415 associated with the region of tissue 411 is illustrated. A region of tissue 419 that did not respond to immunotherapy is illustrated. Region of tissue 419 includes a plurality of cellular nuclei. A global nuclear CG 420 associated with the region of tissue 419 is also illustrated.

Operations 100 also includes, at 150, providing the set of nuclear radiomic features and the set of CG features to a machine learning classifier. In one embodiment, the machine learning classifier is a QDA classifier. In another embodiment, other types of machine learning classifiers, including a linear discriminant analysis (LDA) classifier, a random forest classifier, or a deep learning classifier, including a CNN, may be employed. Providing the set of nuclear radiomic features and the set of CG features to the machine learning classifier includes acquiring electronic data, reading from a computer file, receiving a computer file, reading from a computer memory, or other computerized activity not practically performed in a human mind.

Operations 100 also includes, at 160, receiving, from the machine learning classifier, a probability that the ROT will respond to immunotherapy. The machine learning classifier computes the probability based, at least in part, on the set of nuclear radiomic features and the set of CG features. Receiving the probability includes acquiring electronic data, reading from a computer file, receiving a computer file, reading from a computer memory, or other computerized activity not practically performed in a human mind.

Operations 100 also includes, at 170, generating a classification of the ROT as a responder or non-responder based on the probability. The classification is generated, based, at least in part, on the probability. For example, embodiments may classify the region of tissue as likely to respond to immunotherapy when the probability $>=0.5$, and may classify the region of tissue as unlikely to respond to immunotherapy when the probability $<0.5$. Other classification schemes may be employed. In one embodiment, the classification is further based on the digitized image. Generating the classification includes acquiring electronic data, reading from a computer file, receiving a computer file, reading from a computer memory, or other computerized activity not practically performed in a human mind.

Operations 100 further includes, at 180 displaying the classification. Displaying the classification may include displaying the classification on a computer monitor, a smartphone display, a tablet display, or other displays. Displaying the classification may also include printing the classification. Displaying the classification may also include controlling an immunotherapy response prediction system, a personalized medicine system, a monitor, or other display, to display operating parameters or characteristics of a machine learning classifier, during both training and testing of the machine learning classifier, or during clinical operation of the machine learning classifier. By displaying the classification example embodiments provide a timely and intuitive way for a human medical practitioner to more accurately classify a region of tissue represented in digitized imagery as likely to respond to immunotherapy, or unlikely to respond to immunotherapy, thus improving on existing approaches to predicting response to immunotherapy. Embodiments may further display operating parameters of the machine learning classifier. Embodiments may further display the set of CG features, the set of nuclear radiomic features, the at least one CG, or the digitized image.

While FIG. 1 illustrates various actions occurring in serial, it is to be appreciated that various actions illustrated in FIG. 1 could occur substantially in parallel. By way of illustration, a first process could involve accessing a digitized H&E stained image, a second process could involve extracting radiomic features from a cellular nucleus represented in the image, and a third process could involve constructing a cell graph. While three processes are described, it is to be appreciated that a greater or lesser number of processes could be employed and that lightweight processes, regular processes, threads, and other approaches could be employed.

Figure 10:
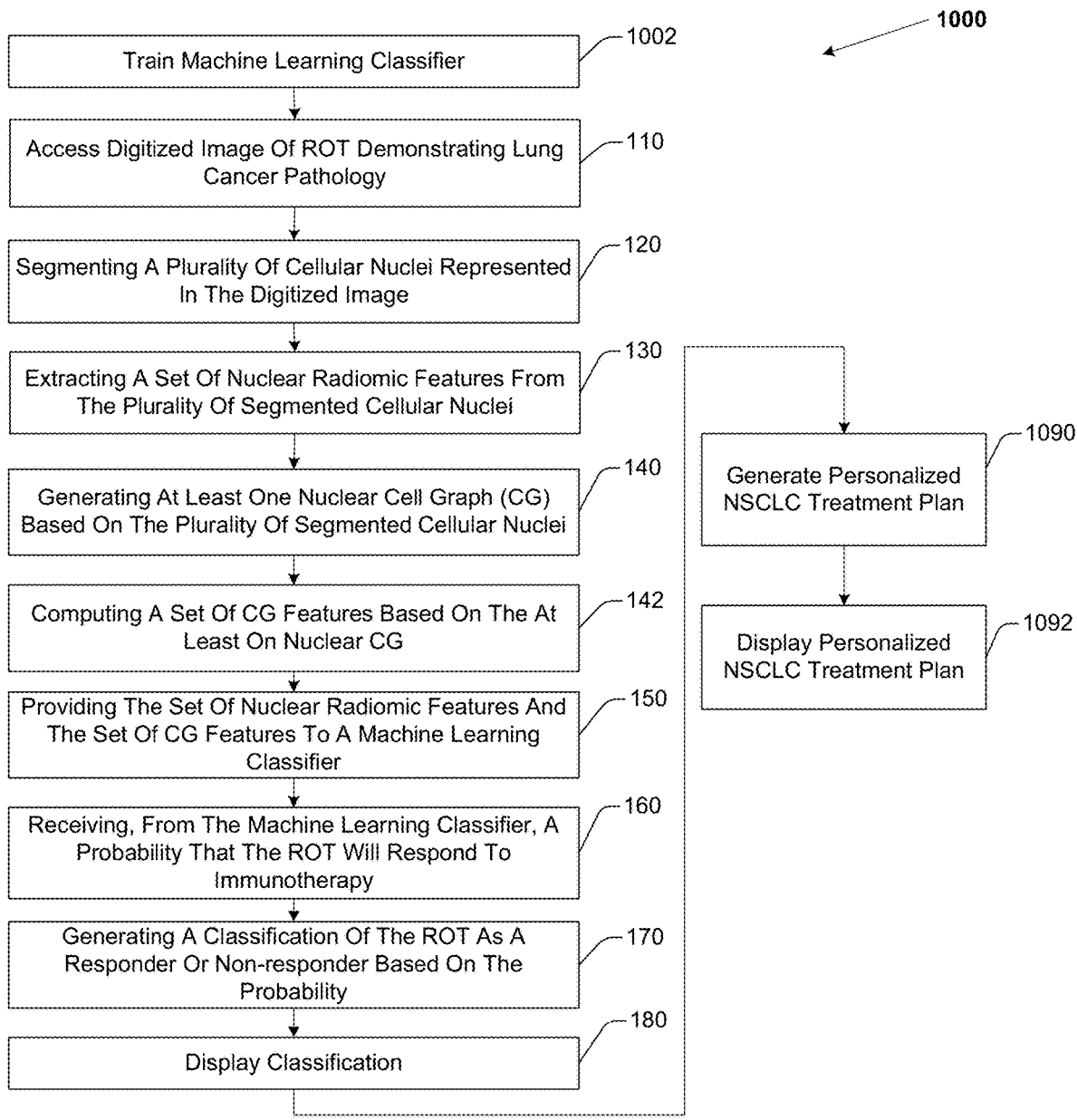
FIG. 10 illustrates an example method for predicting response to immunotherapy in NSCLC.
Figure 11:
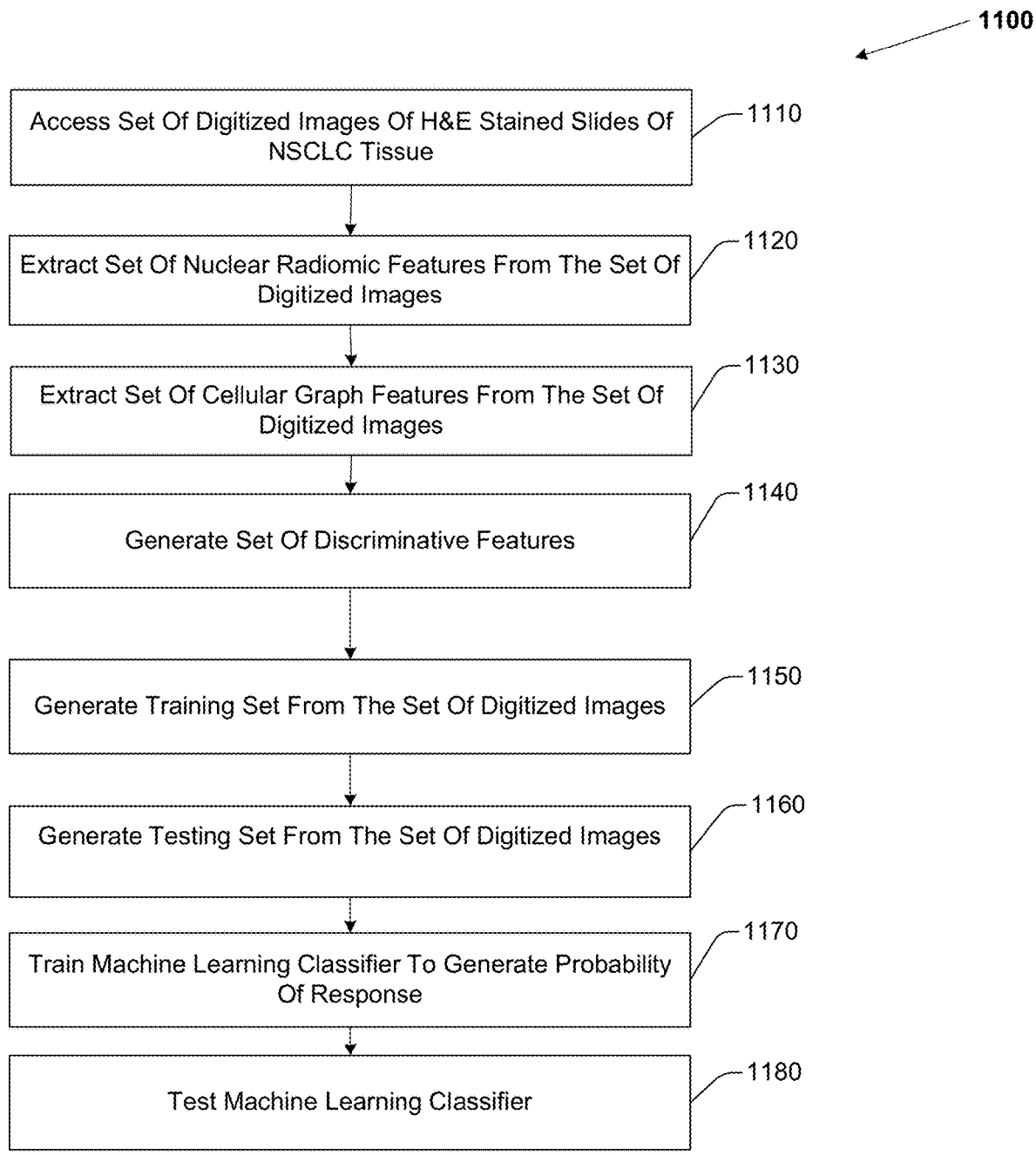
FIG. 11 illustrates operations for training a machine learning classifier to predict response to immunotherapy in NSCLC.

FIG. 10 illustrates a set of operations 1000 that is similar to operations 100 but that includes additional details and elements. Operations 1000 include, at 1002, training the machine learning classifier to compute the probability that a region of tissue will respond to immunotherapy. FIG. 11 illustrates operations 1100 for training the machine learning classifier. In one embodiment, operations 1100 include, at 1110, accessing a set of digitized images of H&E stained slides of NSCLC tissue scanned at 20× magnification, where a digitized image includes a plurality of pixels, a pixel having an intensity, where the set of digitized images includes images of patients who had immunotherapy, where a response status of the patient is known. Members of the set of digitized images may be acquired from different institutions, may be acquired using different scanners, different staining parameters, or at different magnifications.

Operations 1100 also includes, at 1120, extracting a set of nuclear radiomic features from the set of digitized images. Extracting the set of nuclear radiomic features includes acquiring electronic data, reading from a computer file, receiving a computer file, reading from a computer memory, or other computerized activity not practically performed in a human mind. The set of nuclear radiomic features may include at least one of a nuclear size feature, a nuclear area feature, a nuclear axis length feature, a nuclear perimeter feature, or a nuclear texture feature. In one embodiment, the set of nuclear radiomic features includes a standard deviation of the fractal dimension of a nucleus feature, and a mean of a tensor contrast entropy of cellular nuclei feature.

Operations 1100 also includes, at 1130, extracting a set of cellular graph (CG) features from the set of digitized images. In one embodiment, the set of CG features includes at least one of a Delaunay triangulation feature or a Voronoi feature. In one embodiment, the set of CG features includes a side length disorder of a Delaunay triangulation feature, a ratio of minimum and maximum triangular areas formed by nodes of the CG, and a number of possible polygons formed by nodes of the CG. In this embodiment, a polygon is a triangle. Extracting the set of CG features may include constructing at least one CG based on segmented cellular nuclei represented in a member of the set of digitized images according to embodiments described herein. Extracting the set of CG features includes acquiring electronic data, reading from a computer file, receiving a computer file, reading from a computer memory, or other computerized activity not practically performed in a human mind.

Operations 1100 also includes, at 1140, generating a set of discriminative features by selecting a threshold number of the most discriminatory radiomic features and cellular graph features that discriminate response to immunotherapy from non-response to immunotherapy. In one embodiment, the set of discriminative features is selected using an mRMR feature selection approach. In another embodiment, another, different feature selection approach may be employed. In one embodiment, the set of discriminative features includes five features. Generating the set of discriminative features includes acquiring electronic data, reading from a computer file, receiving a computer file, reading from a computer memory, or other computerized activity not practically performed in a human mind.

Operations 1100 also includes, at 1150, generating a training set. The training set is a first subset of the set of digitized images. The training set includes at least one image acquired of a patient that responded to immunotherapy, and at least one image acquired of a patient that did not respond to immunotherapy. Generating the training set includes acquiring electronic data, reading from a computer file, receiving a computer file, reading from a computer memory, or other computerized activity not practically performed in a human mind.

Operations 1100 also includes, at 1160, generating a testing set. The testing set is a second, disjoint subset of the set of digitized images. The testing set includes at least one image acquired of a patient that responded to immunotherapy, and at least one image acquired of a patient that did not respond to immunotherapy. Generating the testing set includes acquiring electronic data, reading from a computer file, receiving a computer file, reading from a computer memory, or other computerized activity not practically performed in a human mind.

Operations 1100 also includes, at 1170, training the machine learning classifier to generate a probability of response using the training set and the set of discriminative features. Training the machine learning classifier may also include determining which features are most discriminative in distinguishing tissue likely to respond to from tissue unlikely to respond. Embodiments may adjust the set of discriminative features based on a desired training time, a desired predictive accuracy, or desired execution time. Adjusting the set of discriminative features may include selecting more than five features, or fewer than five features, or selecting different features for inclusion in the set of discriminative features. Training the machine learning classifier may also include determining settings outside the machine learning classifier architecture but relevant to its learning behavior. Training the machine learning classifier includes acquiring electronic data, reading from a computer file, receiving a computer file, reading from a computer memory, or other computerized activity not practically performed in a human mind.

Operations 1100 further includes, at 1180, testing the machine learning classifier using the testing set and the set of discriminative features. The machine learning classifier is, in one embodiment, evaluated using a concordance index. Testing the machine learning classifier includes acquiring electronic data, reading from a computer file, receiving a computer file, reading from a computer memory, or other computerized activity not practically performed in a human mind.

Returning to FIG. 1000, the set of operations 1000 may also include, at 1090, generating a personalized cancer treatment plan. The personalized cancer treatment plan may be generated based, at least in part, on the classification and at least one of the probability, the set of nuclear radiomic features, the set of CG features, or the digitized image. The personalized cancer treatment plan may be generated for the patient of whom the digitized image was acquired based, at least in part, on the classification, the digitized image, or the set of radiomic features. Defining a personalized cancer treatment plan facilitates delivering a particular treatment that will be therapeutically active to the patient, while minimizing negative or adverse effects experienced by the patient. For example, the personalized cancer treatment plan may suggest a surgical treatment, may define an immunotherapy agent dosage or schedule, or a chemotherapy agent dosage or schedule, for a patient identified as likely to respond to immunotherapy. For a patient classified as unlikely to respond to immunotherapy, other treatments may be suggested. Generating the personalized cancer treatment plan includes acquiring electronic data, reading from a computer file, receiving a computer file, reading from a computer memory, or other computerized activity not practically performed in a human mind. The set of operations 1000 may further include, at 1092, displaying the personalized cancer treatment plan.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 100, 1000, or 1100, method 1200, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved prediction of response may produce the technical effect of improving the administration of chemotherapy or immunotherapy, by increasing the accuracy of and decreasing the time required to determine if a patient is likely or unlikely to respond. Treatments and resources, including expensive immunotherapy or chemotherapy agents may be more accurately tailored to patients with a likelihood of benefiting from said treatments and resources, including responding to immunotherapy, so that more appropriate treatment protocols may be employed, and expensive resources are not wasted, when digitized H&E images are more accurately and more quickly assessed for likelihood of response. Controlling a response prediction apparatus based on improved, more accurate analysis of digitized H&E images further improves the operation of the system, processor, or apparatus, since the accuracy of the system, processor, or apparatus is increased and unnecessary operations will not be performed. Embodiments described herein, including at least operations 100, 1000, or 1100, method 1200, or apparatus 700 or 800, resolve features extracted from digitized H&E imagery at a higher order or higher level than a human can resolve in the human mind or with pencil and paper. For example, properties of the digitized H&E image that are not perceivable by the human eye may be detected by embodiments. Radiomic features generated by embodiments are not properties of tumoral tissue that are perceivable by the human eye, and their computation is not practically performed in the human mind. Nuclear cell graphs are also not a property of tissue represented in the digitized H&E imagery. A machine learning classifier as described herein may not be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Figure 6:
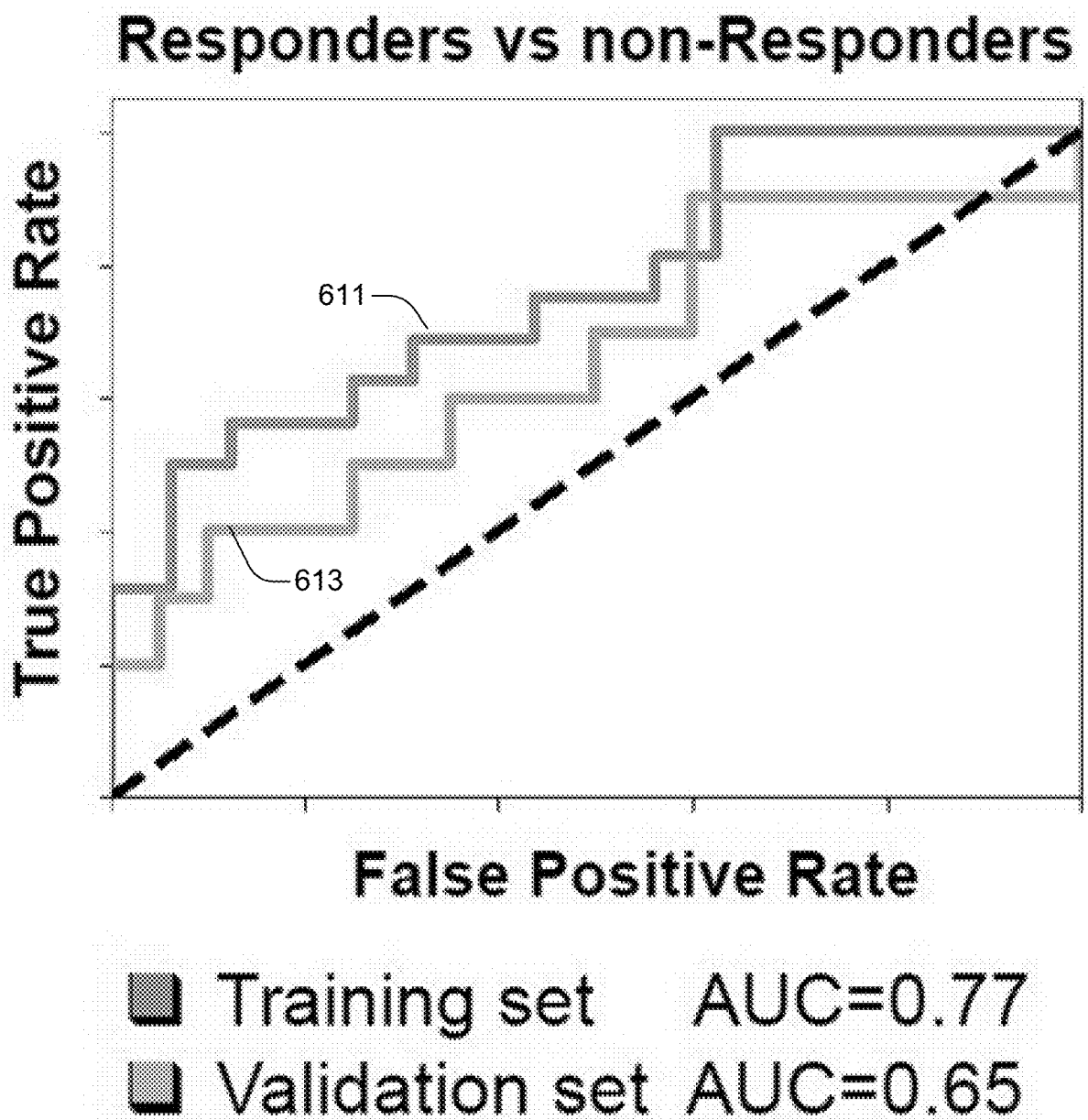
FIG. 6 illustrates area under the curve graphs for predicting response to immunotherapy in NSCLC according to embodiments.

FIG. 6 illustrates area under the receiver operating characteristic (AUC) curves for embodiments described herein. FIG. 6 illustrates the AUC curve 611 for embodiments trained on a training set as described herein. FIG. 6 also illustrates the AUC curve 613 for embodiments tested on a testing set as described herein. Embodiments predict response to immunotherapy based on radiomic and global graph features extracted from digitized H&E stained imagery with an AUC of at least 0.65, thus improving on existing approaches which may predict response to immunotherapy with less accuracy.

Figure 7:
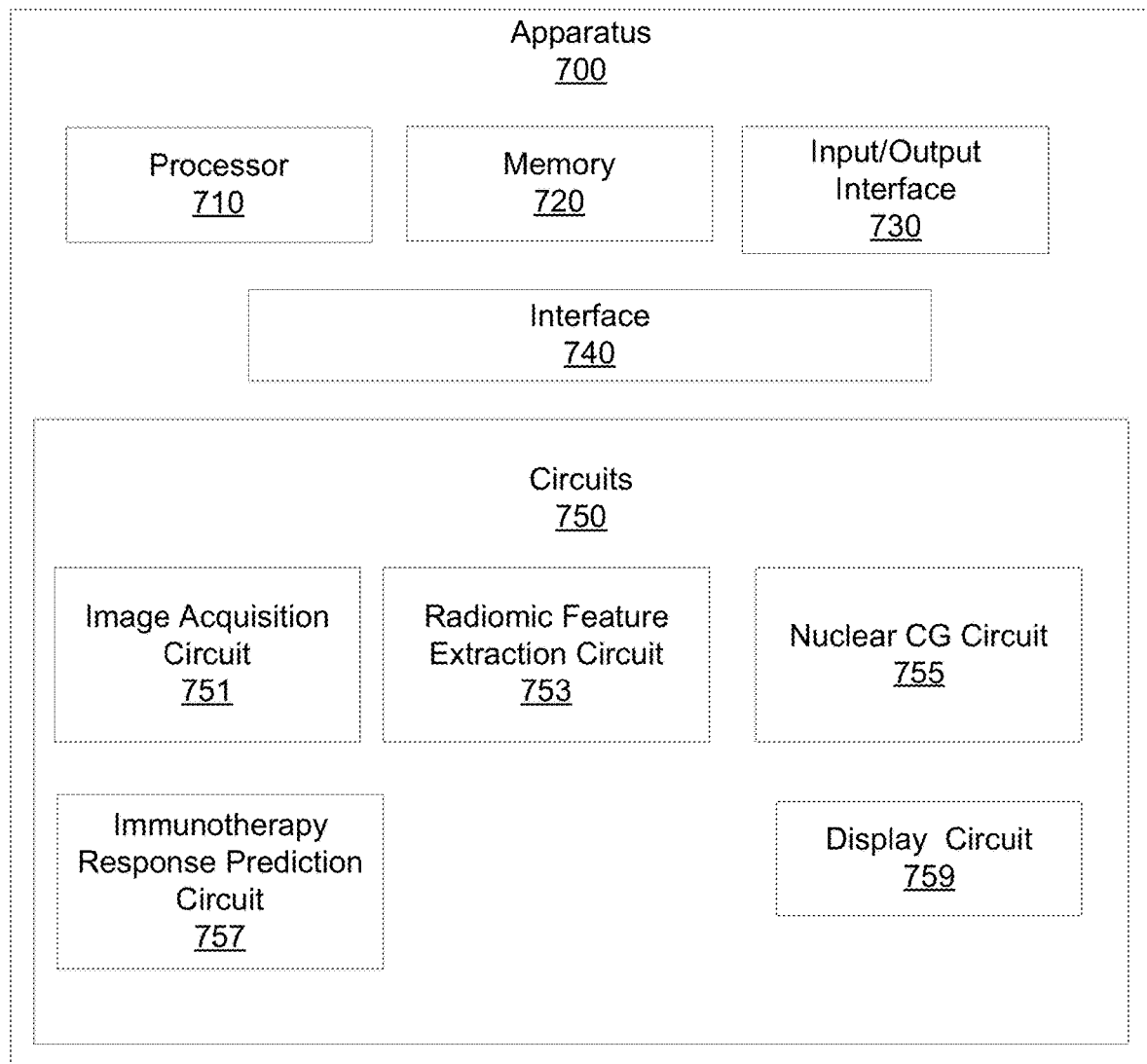
FIG. 7 illustrates an example apparatus for predicting response to immunotherapy in NSCLC.

FIG. 7 illustrates an example apparatus 700. Apparatus 700 may be configured to predict response to immunotherapy in patients demonstrating NSCLC, including early-stage NSCLC. Apparatus 700 includes a processor 710. Apparatus 700 also includes a memory 720. Processor 710 may, in one embodiment, include circuitry such as, but not limited to, one or more single-core or multi-core processors. Processor 710 may include any combination of general-purpose processors and dedicated processors (e.g., graphics processors, application processors, etc.). The processors may be coupled with or may include memory (e.g. memory 720) or storage and may be configured to execute instructions stored in the memory 720 or storage to enable various apparatus, applications, or operating systems to perform the operations. Memory 720 is configured to store a digitized image of a region of tissue demonstrating NSCLC. The digitized image has a plurality of pixels, a pixel having an intensity. Memory 720 may be further configured to store a training set of digitized images, or a testing set of digitized images. Memory 720 may be further configured to store metadata associated with digitized images, including response status data, overall survival (OS) data, or disease free survival (DFS) data associated with patients of whom the imagery is acquired.

Apparatus 700 also includes an input/output (I/O) interface 730, a set of circuits 750, and an interface 740 that connects the processor 710, the memory 720, the I/O interface 730, and the set of circuits 750. I/O interface 730 may be configured to transfer data between memory 720, processor 710, circuits 750, and external devices, for example, a digital whose slide scanner, an immunotherapy response prediction system, or a personalized medicine system.

The set of circuits 750 includes an image acquisition circuit 751, a radiomic feature circuit 753, a nuclear cell graph (CG) circuit 755, an immunotherapy response prediction circuit 757, and a display circuit 759. Image acquisition circuit 751 is configured to access a digitized image of a region of tissue (ROT) demonstrating cancerous pathology, where the ROT includes a plurality of cellular nuclei. The digitized image has a plurality of pixels, a pixel having an intensity. In one embodiment the digitized image is a digitized image of an H&E stained slide of a region of tissue demonstrating NSCLC scanned at 20× magnification. In another embodiment, other, different magnification levels, or other, different types of image of tissue demonstrating NSCLC may be accessed or employed. Accessing the digitized image may include accessing a digitized image stored in memory 720. In one embodiment, accessing the digitized image may include accessing a digitized image stored in a data storage device, including a hard disk drive, a solid state device, a tape drive, or accessing a radiological image over a local area network. Accessing the digitized image includes acquiring electronic data, reading from a computer file, receiving a computer file, reading from a computer memory, or other computerized activity not practically performed in the human mind.

Image acquisition circuit 751 is further configured to segment a plurality of cellular nuclei represented in the digitized image. In one embodiment, image acquisition circuit 751 is configured to segment the plurality of cellular nuclei using a deep learning approach. In another embodiment, image acquisition circuit 751 is configured to segment the plurality of cellular nuclei using a different segmentation technique. In another embodiment, image acquisition circuit 751 is configured to access a digitized image in which a member of the plurality of cellular nuclei is already segmented.

Radiomic feature circuit 753 is configured to extract a set of nuclear radiomic features from the plurality of segmented cellular nuclei. In one embodiment, the set of nuclear radiomic features includes a standard deviation of the fractal dimension of a nucleus feature, and a mean of a tensor contrast entropy of cellular nuclei feature. In another embodiment, the set of nuclear radiomic features includes at least one of a nuclear size feature, a nuclear area feature, a nuclear axis length feature, a nuclear perimeter feature, or a nuclear texture feature. In another embodiment, the set of nuclear radiomic features may include other, different radiomic features.

Nuclear CG circuit 755 is configured to generate at least one nuclear CG based on the plurality of segmented cellular nuclei. A node of the at least one nuclear CG is defined on a centroid of a member of the plurality of cellular nuclei. A first node is connected to a second, different node based on a Euclidean distance between the first node and the second node. In one embodiment, nuclear CG circuit 755 is configured to group individual cell nuclei into clusters. The centroid of a cluster is used as a node and used to form a globally connected graph, where the probability of a link between nodes is inversely proportional to the Euclidean distance between nodes.

Nuclear CG circuit 755 is further configured to compute a set of CG features based on the at least one nuclear CG. In one embodiment, the set of CG features includes a side length disorder of a Delaunay triangulation, a ratio of minimum and maximum triangular areas formed by nodes of the CG, and a number of possible triangles formed by nodes of the CG. In another embodiment, the set of CG features includes at least one of a Delaunay triangulation feature or a Voronoi feature. In another embodiment, the set of CG features may include other, different CG features, or statistical features computed based on the at least one nuclear CG.

Immunotherapy response classification circuit 757 is configured to compute a probability that the ROT will respond to immunotherapy based, at least in part, on the set of nuclear radiomic features and the set of CG features. Immunotherapy response classification circuit 757 is further configured to generate a classification of the ROT as a responder or non-responder based on the probability. In one embodiment, immunotherapy response classification circuit 757 is configured to compute the probability that the region of tissue will respond to immunotherapy using a quadratic discriminant analysis (QDA) machine learning approach. In another embodiment, immunotherapy response classification circuit 757 is configured to compute the probability using another, different machine learning approach (e.g., LDA, random forest, neural networks). Immunotherapy response classification circuit 757 may further be configured to compute a probability that the patient of whom the digitized image is acquired will respond to immunotherapy, or to generate a patient-wise classification of the patient as a responder or non-responder, based, at least in part, on the probability.

Display circuit 759 is configured to display the classification. Display circuit 759 is further configured to display at least one of the probability, the set of nuclear radiomic features, the set of CG features, the CG, or the digitized image. Displaying the classification or at least one of the probability, the set of nuclear radiomic features, the set of CG features, the CG, or the digitized image may also include printing the classification or at least one of the probability, the set of nuclear radiomic features, the set of CG features, the CG, or the digitized image.

Figure 8:
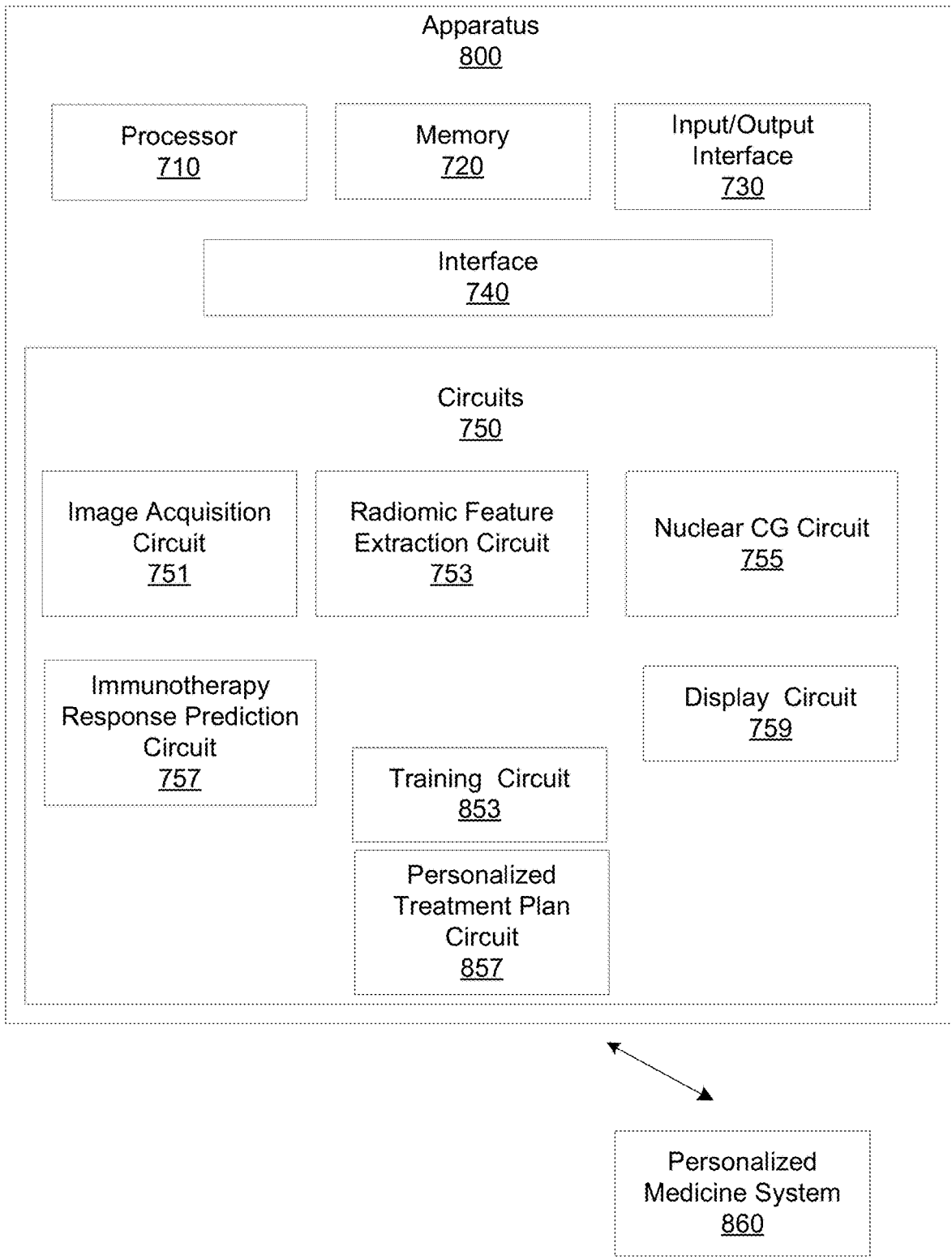
FIG. 8 illustrates an example apparatus for predicting response to immunotherapy in NSCLC.

FIG. 8 illustrates an example apparatus 800 that is similar to apparatus 700 but that includes additional details and elements. In one embodiment, apparatus 800 includes a training circuit 853. Training circuit 853 may be configured to train immunotherapy response classification circuit 757, a machine learning classifier, including a QDA, to classify a region of tissue demonstrating NSCLC according to techniques described herein. In one embodiment, training circuit 853 is configured to access a set of digitized H&E stained images of tissue demonstrating NSCLC pathology, and where the tissue includes a tumoral region. A digitized H&E stained image includes a plurality of pixels, a pixel having an intensity, where a response status for each patient, respectively, is known.

In this embodiment, training circuit 853 is configured to extract a set of nuclear radiomic features from the set of digitized images. Training circuit 853 is also configured to extract a set of cellular graph features from the set of digitized images. Training circuit 853 is also configured to generate a set of discriminative features by selecting a threshold number of the most discriminatory radiomic features and cellular graph features that discriminate response to immunotherapy from non-response to immunotherapy. In one embodiment, training circuit 853 is configured to use an mRMR feature selection approach. In another embodiment, training circuit 853 is configured to use another, different feature selection approach. In one embodiment, the set of discriminative features includes a side length disorder of a Delaunay triangulation, a ratio of minimum and maximum triangular areas formed by nodes of the CG, and a number of possible triangles formed by nodes of the CG. In another embodiment, the set of discriminative features includes at least one of a Delaunay triangulation feature or a Voronoi feature. In one embodiment, the set of discriminative features also includes a standard deviation of the fractal dimension of a nucleus feature, and a mean of a tensor contrast entropy of cellular nuclei feature. In another embodiment, the set of discriminative features includes at least one of a nuclear size feature, a nuclear area feature, a nuclear axis length feature, a nuclear perimeter feature, or a nuclear texture feature.

Training circuit 853 is also configured to generate a training set. The training set is a first subset of the set of images, where the training set includes at least one image acquired of a patient that responded to immunotherapy, and at least one image acquired of a patient that did not respond to immunotherapy.

Training circuit 853 is also configured to generate a testing set. The testing set is a second, disjoint subset of the set of images, where the testing set includes at least one image acquired of a patient that responded to immunotherapy, and at least one image acquired of a patient that did not respond to immunotherapy.

Training circuit 853 is also configured to train the machine learning classifier, including immunotherapy response classification circuit 757, to generate a probability of response using the training set and the set of discriminative features. Training circuit 853 is further configured to test the machine learning classifier, including immunotherapy response classification circuit 757, using the testing set and the set of discriminative features.

Training circuit 853 may be configured to train immunotherapy response classification circuit 757 or test immunotherapy response classification circuit 757 until a threshold level of accuracy or loss is achieved, until a threshold time has been spent training immunotherapy response classification circuit 757, until a threshold amount of computational resources have been expended training immunotherapy response classification circuit 757, until a user terminates training, or some combination thereof. Other training termination conditions may be employed. Once immunotherapy response classification circuit 757 has been trained, it can be applied to new imaging data without repeating training, however training may optionally be repeated in order to make adjustments to immunotherapy response classification circuit 757 given a new set of training data, for example to improve performance among images acquired with a different type of H&E staining, magnification level, or at a different medical institution.

Apparatus 800 also includes personalized treatment plan circuit 857. Personalized treatment plan circuit 857 is configured to generate a personalized NSCLC treatment plan based, at least in part, on the classification. The personalized treatment plan circuit 857 may be further configured to generate the personalized NSCLC treatment plan based the digitized image, the nuclear CG, or the set of radiomic features. Personalized treatment plan circuit 857 may be configured to generate a personalized NSCLC treatment plan for the patient of whom the digitized image was acquired based, at least in part, on the classification, the digitized image, the nuclear CG, or the set of radiomic features. Defining a personalized NSCLC treatment plan facilitates delivering a particular treatment that will be therapeutically active to the patient, while minimizing negative or adverse effects experienced by the patient. For example, the personalized NSCLC treatment plan may suggest a surgical treatment, may define an immunotherapy agent dosage or schedule, or a chemotherapy agent dosage or schedule, for a patient identified as likely to respond to immunotherapy. For a patient classified as unlikely to respond to immunotherapy, other treatments may be suggested.

FIG. 8 further illustrates personalized medicine system 860. Apparatus 800 may be configured to provide the classification, the digitized image, the set of nuclear radiomic features, the nuclear CG graph, or other data to personalized medicine system 860. Personalized medicine system 860 may be, for example, a computer assisted diagnosis (CADx) system, an NSCLC immunotherapy response prediction system, or other type of personalized medicine device that may be used to facilitate the prediction of response to immunotherapy. In one embodiment, personalized treatment plan circuit 857 may control personalized medicine system 860 to display the personalized NSCLC treatment plan, the digitized image, the nuclear CG graph, or the set of radiomic features on a computer monitor, a smartphone display, a tablet display, or other displays.

Figure 9:
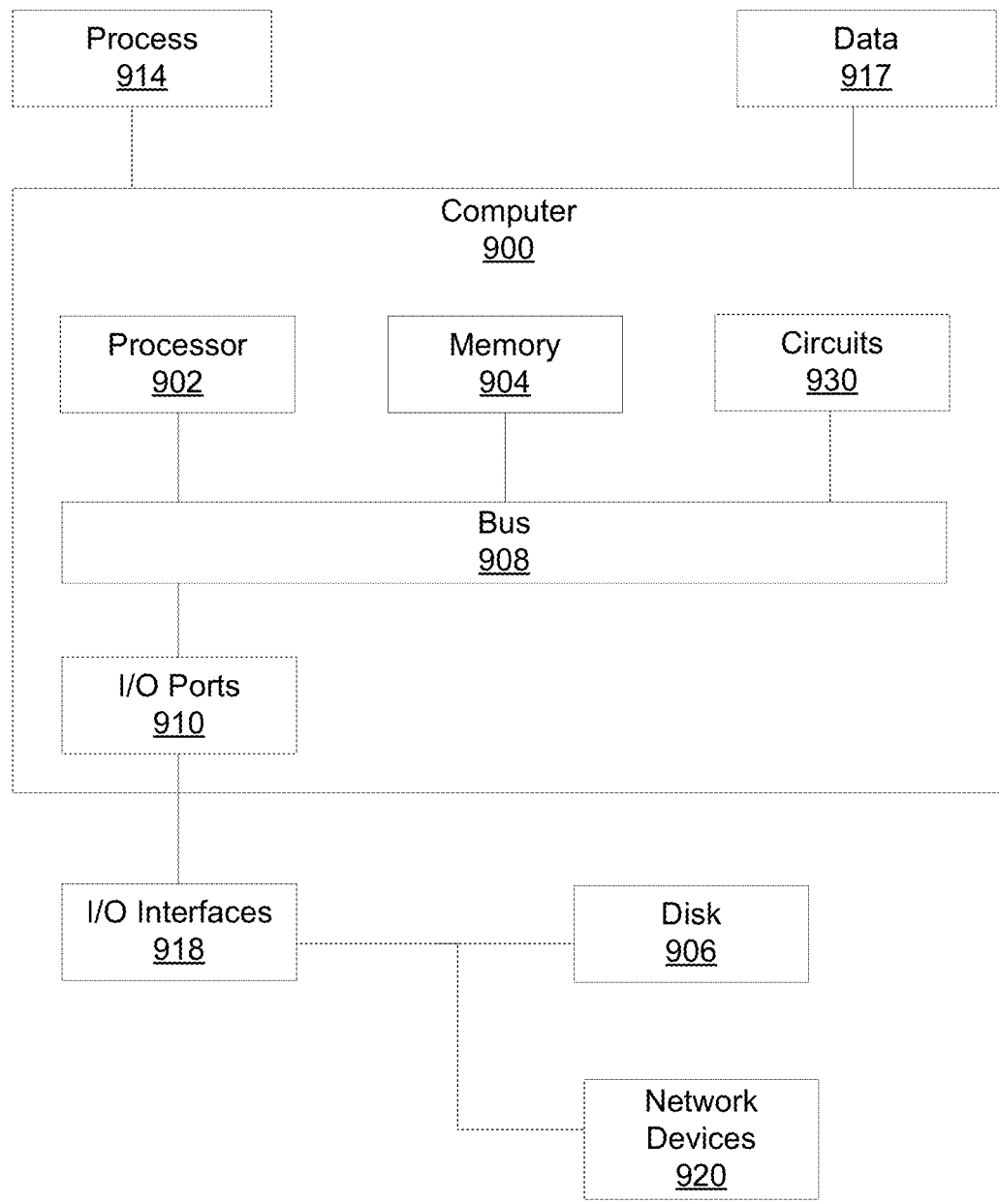
FIG. 9 illustrates an example computer in which embodiments described herein may operate.

FIG. 9 illustrates an example computer 900 in which example methods illustrated herein can operate and in which example methods, apparatus, circuits, operations, or logics may be implemented. In different examples, computer 900 may be part of an NSCLC immunotherapy response prediction system or apparatus, a personalized medicine device, or a digital whole slide scanner, or may be operably connectable to an NSCLC immunotherapy response prediction system or apparatus, a personalized medicine device, or a digital whole slide scanner.

Computer 900 includes a processor 902, a memory 904, and input/output (I/O) ports 910 operably connected by a bus 908. In one example, computer 900 may include a set of logics or circuits 930 that perform operations for or a method of predicting response to immunotherapy, using a machine learning classifier. Thus, the set of circuits 930, whether implemented in computer 900 as hardware, firmware, software, and/or a combination thereof may provide means (e.g., hardware, firmware, circuits) for performing NSCLC immunotherapy prediction based on digitized H&E stained imagery of tissue demonstrating NSCLC. In different examples, the set of circuits 930 may be permanently and/or removably attached to computer 900.

Processor 902 can be a variety of various processors including dual microprocessor and other multi-processor architectures. Processor 902 may be configured to perform steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Data 917 may, in one embodiment, include digitized H&E stained images, CT images, DCE-MRI images, or other type of imagery, or metadata associated with the data 917. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 794, USB, Ethernet).

Computer 900 may interact with input/output devices via I/O interfaces 918 and input/output ports 910. Input/output devices can include, but are not limited to, CT systems, MRI systems, digital whole slide scanners, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

Figure 12:
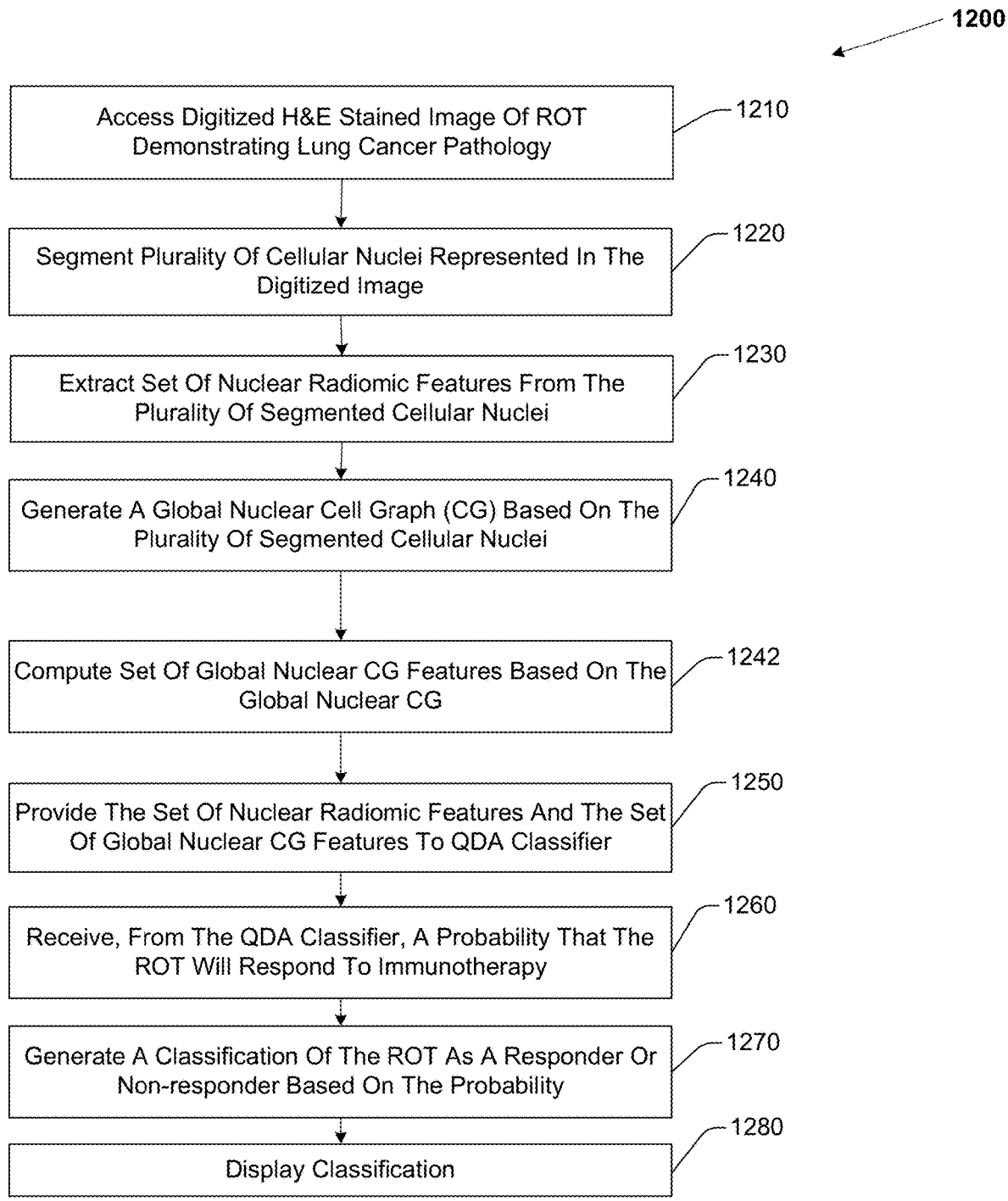
FIG. 12 illustrates a method for predicting response to immunotherapy in NSCLC.

FIG. 12 illustrates a method 1200 for predicting response to immunotherapy in NSCLC. Method 1200 includes, at 1210, accessing a digitized image of a region of tissue (ROT) demonstrating NSCLC pathology. The ROT includes a plurality of cellular nuclei. The digitized image includes a plurality of pixels, a pixel having an intensity. Accessing the digitized image includes acquiring electronic data, reading from a computer file, receiving a computer file, reading from a computer memory, or other computerized activity not practically performed in a human mind.

Method 1200 also includes, at 1220, segmenting a plurality of cellular nuclei represented in the digitized image. The plurality of cellular nuclei may be segmented, in one embodiment, using a deep learning approach. Segmenting the plurality of cellular nuclei includes acquiring electronic data, reading from a computer file, receiving a computer file, reading from a computer memory, or other computerized activity not practically performed in a human mind.

Method 1200 also includes, at 130, extracting a set of shape and texture features from the plurality of segmented cellular nuclei. In one embodiment, the set of shape and texture features includes a standard deviation of the fractal dimension of a nucleus feature, and a mean of a tensor contrast entropy of cellular nuclei feature. In another embodiment, the set of shape and texture features includes at least one of a nuclear size feature, a nuclear area feature, a nuclear axis length feature, a nuclear perimeter feature, or a nuclear texture feature. In another embodiment, the set of shape and texture features may include other, different radiomic features. Extracting the set of shape and texture features includes acquiring electronic data, reading from a computer file, receiving a computer file, reading from a computer memory, or other computerized activity not practically performed in a human mind.

Method 1200 also includes, at 1240, generating a global cell graph (CG) based on the plurality of segmented cellular nuclei. A member of the plurality of segmented nuclei defines a node of the global CG. Generating the global CG graph includes acquiring electronic data, reading from a computer file, receiving a computer file, reading from a computer memory, or other computerized activity not practically performed in a human mind.

Method 1200 also includes, at 1242, computing a set of global CG features based on the global CG. The set of global CG features includes a side length disorder of a Delaunay triangulation, a ratio of minimum and maximum triangular areas formed by nodes of the global CG, and a number of possible triangles formed by nodes of the global CG. In another embodiment, the set of global CG features may include other numbers of features, or other, different global CG features. Computing the set of global CG features includes acquiring electronic data, reading from a computer file, receiving a computer file, reading from a computer memory, or other computerized activity not practically performed in a human mind.

Method 1200 also includes, at 1250, providing the set of shape and texture features and the set of global CG features to a quadratic discriminant analysis (QDA) classifier. The QDA classifier is trained to distinguish responders to immunotherapy from non-responders to immunotherapy. Providing the set of shape and texture features and the set of global CG features to the QDA classifier includes acquiring electronic data, reading from a computer file, receiving a computer file, reading from a computer memory, or other computerized activity not practically performed in a human mind.

Method 1200 also includes, at 1260, receiving, from the QDA classifier, a probability that the ROT will respond to immunotherapy. The QDA computes the probability based, at least in part, on the set of shape and texture features and the set of global CG features. Receiving the probability includes acquiring electronic data, reading from a computer file, receiving a computer file, reading from a computer memory, or other computerized activity not practically performed in a human mind.

Method 1200 also includes, at 1270, generating a classification of the ROT as a responder or non-responder based on the probability. Generating the classification of the ROT as a responder or non-responder may also include generating a classification of the patient of whom the digitized image was acquired as a responder or non-responder based on the probability. Generating the classification includes acquiring electronic data, reading from a computer file, receiving a computer file, reading from a computer memory, or other computerized activity not practically performed in a human mind.

Method 1200 further includes, at 1280, displaying the classification. Displaying the classification includes acquiring electronic data, reading from a computer file, receiving a computer file, reading from a computer memory, or other computerized activity not practically performed in a human mind. Displaying the classification may further include displaying the digitized image, the global CG, the set of global CG features, the set of shape and texture features, or the probability.

Examples herein can include subject matter such as an apparatus, including an NSCLC immunotherapy response prediction apparatus or system, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting NSCLC immunotherapy response, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that, in response to execution, cause a processor to perform operations comprising:

accessing a digitized image of a region of tissue (ROT) demonstrating cancerous pathology, where the ROT includes a plurality of cellular nuclei, where the digitized image includes a plurality of pixels, a pixel having an intensity;

segmenting a plurality of cellular nuclei represented in the digitized image;

extracting a set of nuclear radiomic features from the plurality of segmented cellular nuclei;

generating at least one nuclear cell graph (CG) based on the plurality of segmented cellular nuclei;

computing a set of CG features based on the at least one nuclear CG;

providing the set of nuclear radiomic features and the set of CG features to a machine learning classifier;

receiving, from the machine learning classifier, a probability that the ROT will respond to immunotherapy, where the machine learning classifier computes the probability based, at least in part, on the set of nuclear radiomic features and the set of CG features;

generating a classification of the ROT as a responder or non-responder based on the probability; and displaying the classification.

2. The non-transitory computer-readable storage device of claim 1, where segmenting the plurality of cellular nuclei represented in the digitized image includes segmenting the plurality of cellular nuclei using a deep learning approach.

3. The non-transitory computer-readable storage device of claim 1, where the set of nuclear radiomic features includes at least one of a nuclear size feature, a nuclear area feature, a nuclear axis length feature, a nuclear perimeter feature, or a nuclear texture feature.

4. The non-transitory computer-readable storage device of claim 1, where the set of nuclear radiomic features includes a standard deviation of the fractal dimension of a nucleus feature, and a mean of a tensor contrast entropy of cellular nuclei feature.

5. The non-transitory computer-readable storage device of claim 1, where a node of the at least one nuclear CG is defined on a centroid of a member of the plurality of cellular nuclei, and where a first node is connected to a second, different node based on a Euclidean distance between the first node and the second node.

6. The non-transitory computer-readable storage device of claim 1, where the at least one nuclear CG is a global CG.

7. The non-transitory computer-readable storage device of claim 1, where the set of CG features includes at least one of a Delaunay triangulation feature or a Voronoi feature.

8. The non-transitory computer-readable storage device of claim 1, where the set of CG features includes a side length disorder of a Delaunay triangulation, a ratio of minimum and maximum triangular areas formed by nodes of the CG, and a number of possible polygons formed by nodes of the CG.

9. The non-transitory computer-readable storage device of claim 8, where a polygon is a triangle.

10. The non-transitory computer-readable storage device of claim 1, where the machine learning classifier is a quadratic discriminant analysis (QDA) classifier.

11. The non-transitory computer-readable storage device of claim 1, the operations further comprising generating a personalized NSCLC treatment plan based on the classification; and
displaying the personalized NSCLC treatment plan.

12. The non-transitory computer-readable storage device of claim 1, where the digitized image is a digitized image of a hematoxylin and eosin (H&E) stained slide of region of tissue demonstrating non-small cell lung cancer (NSCLC) scanned at 20× magnification.

13. The non-transitory computer-readable storage device of claim 1, the operations further comprising training the machine learning classifier to compute the probability that the region of tissue will respond to immunotherapy.

14. The non-transitory computer-readable storage device of claim 13, where training the machine learning classifier comprises:
accessing a set of digitized images of H&E stained slides of NSCLC tissue scanned at 20× magnification, where a digitized image includes a plurality of pixels, a pixel having an intensity, where the set of digitized images includes images of patients who had immunotherapy, where a response status of the patient is known;
extracting a set of nuclear radiomic features from the set of digitized images;
extracting a set of cellular graph features from the set of digitized images;
generating a set of discriminative features by selecting a threshold number of the most discriminatory radiomic features and cellular graph features that discriminate response to immunotherapy from non-response to immunotherapy;
generating a training set where the training set is a first subset of the set of images, where the training set includes at least one image acquired of a patient that responded to immunotherapy, and at least one image acquired of a patient that did not respond to immunotherapy;
generating a testing set where the testing set is a second, disjoint subset of the set of images, where the testing set includes at least one image acquired of a patient that responded to immunotherapy, and at least one image acquired of a patient that did not respond to immunotherapy;
training the machine learning classifier to generate a probability of response using the training set and the set of discriminative features; and
testing the machine learning classifier using the testing set and the set of discriminative features.

15. An apparatus for predicting response to immunotherapy in non-small cell lung cancer (NSCLC), the apparatus comprising:
a processor;
a memory configured to store a digitized image of a region of tissue demonstrating NSCLC, the region of tissue including a plurality of cellular nuclei, the digitized image having a plurality of pixels, a pixel having an intensity;
an input/output (I/O) interface;
a set of circuits; and
an interface that connects the processor, the memory, the I/O interface, and the set of circuits, the set of circuits comprising:
an image acquisition circuit configured to:
access a digitized image of a region of tissue (ROT) demonstrating cancerous pathology, where the ROT includes a plurality of cellular nuclei, where the digitized image includes a plurality of pixels, a pixel having an intensity; and
segment a plurality of cellular nuclei represented in the digitized image;
a radiomic feature circuit configured to:
extract a set of nuclear radiomic features from the plurality of segmented cellular nuclei;
a nuclear cell graph (CG) circuit configured to:
generate at least one nuclear CG based on the plurality of segmented cellular nuclei, where a node of the at least one nuclear CG is defined on a centroid of a member of the plurality of cellular nuclei, and where a first node is connected to a second, different node based on a Euclidean distance between the first node and the second node; and
compute a set of CG features based on the at least one nuclear CG;
an immunotherapy response prediction circuit configured to:
compute a probability that the ROT will respond to immunotherapy based, at least in part, on the set of nuclear radiomic features and the set of CG features; and
generate a classification of the ROT as a responder or non-responder based on the probability; and
a display circuit configured to:
display the classification and at least one of the probability, the set of nuclear radiomic features, the set of CG features, the CG, or the digitized image.

16. The apparatus of claim 15, where the set of nuclear radiomic features includes a standard deviation of the fractal dimension of a nucleus feature, and a mean of a tensor contrast entropy of cellular nuclei feature.

17. The apparatus of claim 15, where the set of CG features includes a side length disorder of a Delaunay triangulation, a ratio of minimum and maximum triangular areas formed by nodes of the CG, and a number of possible triangles formed by nodes of the CG.

18. The apparatus of claim 15, where the immunotherapy response prediction circuit is configured to compute the probability that the region of tissue will respond to immunotherapy using a quadratic discriminant analysis (QDA) machine learning approach.

19. The apparatus of claim 15, where the digitized image is a digitized image of a hematoxylin and eosin (H&E) stained slide of a region of tissue demonstrating NSCLC scanned at 20× magnification.

20. A method for predicting response to immunotherapy in non-small cell lung cancer (NSCLC), the method comprising:

accessing a digitized hematoxylin and eosin (H&E) stained image of a region of tissue (ROT) demonstrating NSCLC pathology, where the ROT includes a plurality of cellular nuclei, where the digitized image includes a plurality of pixels, a pixel having an intensity;

segmenting a plurality of cellular nuclei represented in the digitized H&E stained image using a deep learning approach;

extracting a set of shape and texture features from the plurality of segmented cellular nuclei;

generating a global cell graph (CG) based on the plurality of segmented cellular nuclei, where a member of the plurality of segmented nuclei defines a node of the global CG;

computing a set of global CG features based on the global CG, where the set of global CG features includes a side length disorder of a Delaunay triangulation, a ratio of minimum and maximum triangular areas formed by nodes of the global CG, and a number of possible triangles formed by nodes of the global CG;

providing the set of shape and texture features and the set of global CG features to a quadratic discriminant analysis (QDA) classifier trained to distinguish responders to immunotherapy from non-responders to immunotherapy;

receiving, from the QDA classifier, a probability that the ROT will respond to immunotherapy, where the QDA classifier computes the probability based, at least in part, on the set of shape and texture features and the set of global CG features;

generating a classification of the ROT as a responder or non-responder based on the probability; and displaying the classification.

* * * * *

UNITED STATES PATENT AND TRADEMARK OFFICE
CERTIFICATE OF CORRECTION

PATENT NO. : 11,055,844 B2
APPLICATION NO. : 16/281324
DATED : July 6, 2021
INVENTOR(S) : Anant Madabhushi et al.

Page 1 of 1

It is certified that error appears in the above-identified patent and that said Letters Patent is hereby corrected as shown below:

In the Specification

Column 1, Lines 17 through 24; please replace "This invention was made with government support under the grant(s): 1U24CA199374-01, R01CA202752, R01CA202752-01A1, R01CA208236-01A1, R21CA179327-01, R21CA195152-01, R01 DK098503-02, 1 C06 RR12463-01 and NIH T32EB007509, awarded by the National Institutes of Health. Also PC120857, LC130463, and W81XWH-16-1-0329 awarded by the Department of Defense. The government has certain rights in the invention." with --This invention was made with government support under the grant(s): CA179327, CA195152, DK098503, CA199374, CA202752, CA208236, RR012463, and EB007509, awarded by the National Institutes of Health; and grants W81XWH-13-1-0418, W81XWH-14-1-0323, and W81XWH-16-1-0329 awarded by the Department of Defense. The government has certain rights in the invention.--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*